(12) United States Patent
Bel-Rhlid et al.

(10) Patent No.: US 8,481,028 B2
(45) Date of Patent: Jul. 9, 2013

(54) COMPOSITIONS FOR PREPARING A COFFEE BEVERAGE COMPRISING HYDROLYSED CHLOROGENIC ACID

(75) Inventors: Rachid Bel-Rhlid, Savigny (CH); Karin Kraehenbuehl, Fully (CH); Christophe Cavin, Montreux (CH); Thomas Wolfgang Raab, Grandvaux (CH); Nicolas Page, Lausanne (CH)

(73) Assignee: Nestec S.A., Vevey (CH)

( * ) Notice: Subject to any disclaimer, the term of this patent is extended or adjusted under 35 U.S.C. 154(b) by 108 days.

(21) Appl. No.: 12/990,591

(22) PCT Filed: Mar. 12, 2009

(86) PCT No.: PCT/EP2009/052932
§ 371 (c)(1),
(2), (4) Date: Nov. 1, 2010

(87) PCT Pub. No.: WO2009/132887
PCT Pub. Date: Nov. 5, 2009

(65) Prior Publication Data
US 2011/0044951 A1 Feb. 24, 2011

(30) Foreign Application Priority Data
Apr. 30, 2008 (EP) .................................... 08155449

(51) Int. Cl.
*A01N 63/00* (2006.01)

(52) U.S. Cl.
USPC ......... 424/93.4; 424/93.1; 424/94.1; 424/725

(58) Field of Classification Search
None
See application file for complete search history.

(56) References Cited

U.S. PATENT DOCUMENTS
2006/0257384 A1   11/2006   Molin et al.

FOREIGN PATENT DOCUMENTS
| EP | 0916267 | 5/1999 |
|---|---|---|
| EP | 1069830 | 1/2001 |
| EP | 1726213 | 11/2006 |
| EP | 1872665 | 1/2008 |
| GB | 394621 | 6/1933 |
| JP | 2001321116 | 11/2001 |
| WO | WO 2008/028300 | 3/2008 |

OTHER PUBLICATIONS

Kurkal V. et al., Enzyme Activity and Flexibility at Very Low Hydration, Biophysical Journal, Aug. 2005, vol. 89, pp. 1282-1287.*
Bel-Rhlid R. et al., Hydrolysis of Rosmarinic Acid from Rosemary Extract with Esterases and Lactobacillus johnsonii in Vitro and in a Gastrointestinal Model, J. Agric. Food Chem., 2009, vol. 57, pp. 7700-7705.*
Holzapfel W.H. et al., Taxonomy and important features of probiotic microorganisms in food and nutrition, Am. J.Clin. Nutr., 2001, vol. 73 (suppl), pp. 365S-373S.*
Cavin, et al., "The coffe-specific diterpenes cafestol and kahweol protect against aflatoxin B1-induced genotoxicity through a dual mechanism," Carcinogenesis, vol. 19, No. 8, 1998, pp. 1369-1375.
C. Cavin, et al., "Coffee diterpenes prevent benzo[a]pyrene genotoxicity in rat and human culture systems", Biochemical and Biophysical Research Communications, vol. 306, Issue 2, Jun. 2003, pp. 488-495.
W. Huber, et al., "Enhancement of the chemoprotective enzymes glucuronosyl transferase and glutathione transferase in specific organs of the rat by the coffee components kahweol and cafestol," Archives of Toxicology, vol. 76, No. 4, 2002, pp. 209-217.
H. Steinkellner, et al., "Coffee consumption induces GSTP in plasma and protects lymphocytes against (±)-anti-benzo [a]pyrene-7,8-dihydrodiol-9,10-epoxide induced DNA-damage: Results of controlled human intervention trials," Mutation Research/Fundamental and Molecular Mechanisms of Mutagenesis, vol. 591, Issues 1-2, Dec. 2005, pp. 264-275.
Wang, et al., "Generation of a Stable Antioxidant Response Element-Driven Reporter Gene Cell Line and Its Use to Show Redox-Dependent Activation of Nrf2 by Cancer Chemotherapeutic Agents," Cancer Research, Nov. 2006, vol. 66, pp. 10983-10994.
Cavin, et al., "Induction of Nrf2-mediated cellular defenses and alteration of phase I activities as mechanisms of chemoprotective effects of coffee in the liver," Food and Chemical Toxicology, vol. 46, Issue 4, Apr. 2008, pp. 1239-1248.
Cavin, et al., "Inhibition of the expression and activity of cyclooxygenase-2 by chicory extract," Biochemical and Biophysical Research Communications, vol. 327, Issue 3, Feb. 2005, pp. 742-749.
Sidhu, et al., "Influence of extracellular matrix overlay on phenobarbital-mediated induction of CYP2B1, 2B2, and 3A1 genes in primary adult rat hepatocyte culture," Archives of Biochemistry and Biophysics, vol. 301, Issue 1, Feb. 1993, pp. 103-113.
Couteau, et al., "Isolation and characterization of human colonic bacteria able to hydrolyse chlorogenic acid," Journal of Applied Microbiology, vol. 90, No. 6, 2001, 873-881.
Asther, et al., "Purification and characterization of a chlorogenic acid hydrolase from Aspergillus niger catalysing the hydrolysis of chlorogenic acid," Journal of Biotechnology, vol. 115, Issue 1, Jan. 2005, pp. 47-56.
International Search Report for International Application No. PCT/EP2009/052932 mailed on May 11, 2009.
Written Opinion for International Application No. PCT/EP2009/052932 mailed on May 11, 2009.

* cited by examiner

*Primary Examiner* — Jon P Weber
*Assistant Examiner* — Satyendra Singh
(74) *Attorney, Agent, or Firm* — K&L Gates LLP

(57) ABSTRACT

The invention relates to compositions for preparing a beverage, the compositions comprise a microorganism and/or an enzyme capable of hydrolysing chlorogenic acids of a coffee extract to phenolic acids. When a beverage prepared with the compositions of the invention is consumed chlorogenic acids present in coffee extract is hydrolysed to improve antioxidant and/or anti-inflammatory properties compared to a similar conventional beverage.

6 Claims, 1 Drawing Sheet

COMPOSITIONS FOR PREPARING A COFFEE BEVERAGE COMPRISING HYDROLYSED CHLOROGENIC ACID

FIELD OF THE INVENTION

The present invention relates to compositions for preparing a beverage. The compositions comprise a microorganism and/or an enzyme capable of hydrolysing chlorogenic acids of a coffee extract to phenolic acids. Beverages prepared with the compositions of the invention have improved antioxidant and/or anti-inflammatory properties.

BACKGROUND OF THE INVENTION

Coffee and coffee active compounds such as caffeine and diterpenes (e.g. cafestol, kahweol) have been shown to induce detoxifying enzymes (e.g. glutathione-S-transferases GST) in rodents (Cavin C. et al, 1998. The coffee-specific diterpenes cafestol and kahweol protect against aflatoxin B1-induced genotoxicity trough a dual mechanism. Carcinogenesis 19, 1369-1375; Cavin, C. et al, 2003. Coffee diterpenes prevent benzo[a]pyrene genotoxicity in rat and human culture systems. Biochemical Biophysical Research Communication 306, 488-495; Huber, W. et al. 2002a. Enhancement of the chemoprotective enzymes glucuronyl transferase and glutathione transferase in specific organs of the rat by the coffee components kahweol and cafestol. Archive of Toxicology 76, 209-217). Increased GST activity by coffee has been further demonstrated in human following consumption of 800 ml of coffee for 5 days (Steinkellner, H. et al. 2005. Coffee consumption induces GSTP in plasma and protects lymphocytes against (+/−)-anti-benzo[a] pyrene-7, 8-dihydrodiol-9,10-epoxide induced DNA-damage: results of controlled human intervention trials. Mut. Res. 591 264-275).

This kind of antioxidant activity is known to protect against "oxidative stress" by reducing damaging free radicals that may be implicated e.g. in cancer, heart disease, degenerative brain disorders and ageing.

To increase the health benefits of food and beverage products there is a desire to produce products with an increased antioxidant activity, as well as other beneficial biological activities.

SUMMARY OF THE INVENTION

The inventors have surprisingly found that treating coffee extract with microorganisms or enzymes capable of hydrolysing chlorogenic acids to generate phenolic acids results in improved antioxidant and/or anti-inflammatory properties of the coffee extract. Furthermore, it has been found that this treatment can take place in vivo when a human or an animal ingests a coffee extract in combination with an enzyme or microorganism capable of hydrolysing chlorogenic acids to generate phenolic acids.

Accordingly the present invention relates to a beverage powder comprising: a) a dried coffee extract; and b) a microorganism and/or an enzyme capable of hydrolysing caffeoyl quinic acid and diesters to generate caffeic acid. In a further aspect the invention relates to a kit for preparing a beverage, comprising at least two parts: a) a first part comprising a coffee extract; and b) a second part comprising a microorganism and/or an enzyme capable of hydrolysing chlorogenic acids to generate phenolic acids. In a still further aspect the invention relates to use of the products of the invention.

DETAILED DESCRIPTION OF THE INVENTION

Figure 1:
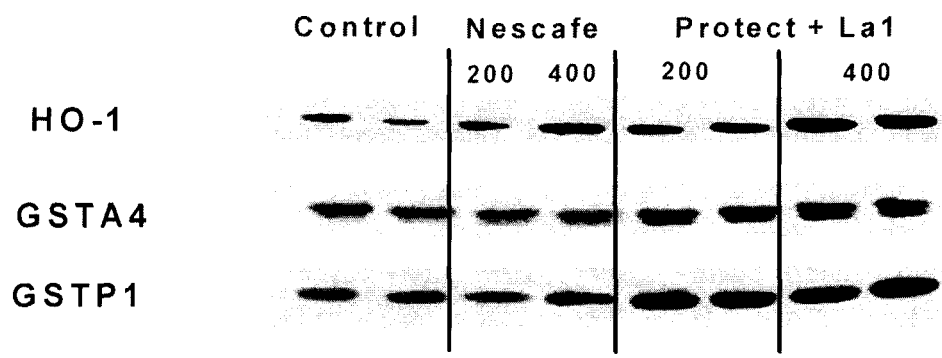
FIG. 1: Western Blot gels showing protein expression of GST subunits (GSTA4, GSTP1) and Heme-Oxygenase-1 (HO-1) in rat primary heptocytes treated with 200 and 400 ug/ml NESCAFE RED CUP® (extract of roasted coffee beans) not treated to hydrolyse chlorogenic acids, and 200 and 400 ug/ml NESCAFE PROTECT® treated with *Lactobacillus johnsonii*, as well as control samples not treated with coffee extract. For details see example 1.

Compositions to be mixed with a coffee extract to prepare a coffee beverage are well known in the art, e.g. milk, cream, coffee whiteners, and coffee creamers. Such compositions are used by consumers to modify e.g. the aroma, appearance and texture of coffee. The compositions may be in liquid or dry form, e.g. as powders, that are dissolved and/or suspended in a cup of coffee, e.g. a cup of freshly brewed coffee or a cup of coffee prepared by dissolving pure soluble coffee in water.

In one embodiment of the invention the composition to be mixed with a coffee extract is a coffee creamer or a coffee whitener. A creamer may e.g. be based on milk protein and/or milk fat, or it may be a non dairy creamer based on vegetable protein and/or vegetable fat. The composition may be in a dry form, e.g. as a powder, wherein the water content is e.g. less than 5%. The composition may also be in a liquid form.

The composition to be mixed with a coffee extract according to the invention comprises a microorganism and/or an enzyme capable of hydrolysing chlorogenic acids to generate phenolic acids. Chlorogenic acids are a family of esters formed between trans-cinnamic acids and quinic acid. Chlorogenic acids are naturally present in coffee, mainly as mono- and di-esters of quinic acid and phenolic groups (e.g. caffeic, ferulic, coumaric, methoxycinnamic) attached to different positions. In one embodiment of the invention the microorganism and/or enzyme is capable of hydrolysing caffeoyl quinic acid and diesters (e.g. 3-, 4-, or 5-caffeoyl quinic acid and diesters), and/or feruloyl quinic acid and diesters (e.g. 3-, 4-, or 5-feruloyl quinic acid and diesters), to generate caffeic acid and ferulic acid, respectively.

The composition of the invention should be formulated such that the microorganism and/or enzyme will not ferment or react with the composition during storage. This may be achieved e.g. by formulating the composition as a dry powder, and/or by encapsulating the microrganism and/or enzyme so that the microorganisms and/or enzyme will only be released when the composition is mixed with coffee extract or during digestion.

The composition of the invention may further comprise any ingredient suitable for inclusion in a composition to be mixed with a coffee extract to prepare a beverage. Usual ingredients may e.g. be sugars, artificial sweeteners, emulsifiers, stabilisers, thickeners, flowing agents, colours, flavours, aromas, and the like. Suitable artificial sweeteners include saccharin, cyclamates, acetosulfame, L-aspartyl based sweeteners such as aspartame, and mixtures of these. Suitable emulsifiers include monoglycerides, diglycerides, lecithin, diacetyl tartaric acid esters of mono-diglycerides, emulsifying starches, and mixtures thereof. Suitable stabilisers include dipotassium phosphate and sodium citrate. A suitable flowing agent is sodium silica aluminate. In one embodiment the composition comprises milk protein and/or vegetable protein. In a further embodiment the composition comprises milk fat and/or vegetable fat.

Coffee Extract

A coffee extract according to the invention is an extract of green coffee beans and/or roasted coffee beans by water or steam. Numerous methods for producing coffee extracts are known in the art, e.g. from EP 0916267. The coffee extract may e.g. be pure soluble coffee. Pure soluble coffee products are readily available and numerous methods for producing pure soluble coffee products are known in the art, e.g. from EP 106930.

Microorganisms

Microorganisms capable of hydrolysing chlorogenic acid may e.g. be identified as disclosed in the examples of this application. Suitable microorganisms may be selected from yeasts, fungi or bacteria. Suitable microorganisms may e.g. be an *Aspergillus*; such as e.g. *Aspergillus oryzae*, a *Lactobacillus*, such as e.g. *L. johnsonii* (CNCM I-1225); a *Bifidobacterium*, such as e.g. *B. lactis* (CNCM I-3446), or a yeast such as e.g. *Saccharomyces cerevisiae*.

Enzymes

A suitable enzyme is e.g. an esterase e.g. a chlorogenate esterase derived from *Aspergillus japonicus*. (Commercially available from Kikkoman, Japan), Tannase from *Aspergillus oryzae* (EC 3.1.1.20) (commercially available from Kikkoman, Japan); and Palatase 20000L (EC 3.1.1.3) (commercially available from Novozymes A/S, Denmark). The enzyme may be present as a purified enzyme or e.g. in the form of a cell lysate of a microorganism. Suitable cells may e.g. be cells of the microroganisms mentioned above. Suitable methods for producing cell lysate are known in the art.

The microorganism and/or enzyme should be present in an amount sufficient for hydrolysing a substantial amount of chlorogenic acids present in the coffee extract to phenolic acids during digestion. The amount of microorganism and/or enzyme needed may e.g. be determined in the TIM digestion model described in Example 3 herein, by determining the amount of chlorogenic acids hydrolysed during the digestion experiment. Preferably at least 20%, such as at least 30%, at least 50%, or at least 75% of caffeoyl quinic acids (CQA) and/or feruloyl quinic acids (FQA) present in the coffee extract is hydrolysed.

Kit of Parts

In one embodiment the invention relates to a kit for preparing a beverage, comprising at least two parts: a) a first part comprising a coffee extract; and b) a second part comprising a microorganism and/or an enzyme capable of hydrolysing chlorogenic acids to generate phenolic acids. The two parts are sold together for the preparation of a beverage but are physically separated in the packing of the product. The final beverage to be consumed is prepared by mixing the two parts shortly before consumption. If one or both parts are in a liquid form they may be mixed directly, optionally further liquid, e.g. water or milk, may be added. The two parts may also be mixed by dissolving or suspending them in a liquid, e.g. water or milk. When liquid is used this may be hot or cold depending on whether a hot or a cold beverage is desired. If hot liquid is used, it may preferably have a temperature which is not so high as to inactivate the microorganism and/or enzyme before ingestion of the beverage.

The first part of the kit comprises a coffee extract. In a preferred embodiment the first part is in a dry form, e.g. in the form of a powder. The coffee extract may e.g. be a conventional pure soluble coffee powder, e.g. a spray dried or freeze dried coffee extract. Pure soluble coffee powders are readily available and extensively described in the art. The first part may also be in a liquid form. Liquid coffee extracts are readily available e.g. as ready-to-drink coffee beverages. The first part may additionally comprise any other suitable ingredient, e.g. chicory extract, aroma additives, stabilisers, salts, and/or sweeteners. The first part may be packed in any suitable way, e.g. in a sachet, bottle or can.

The second part comprises a microorganism and/or an enzyme capable of hydrolysing chlorogenic acids to generate phenolic acids. This part may preferably be in the form of a composition to be mixed with a coffee extract as described herein, preferably in the form of a coffee whitener or coffee creamer. It may comprise any other suitable components, e.g. components usually found in coffee creamers or coffee whiteners, such as the components mentioned herein as ingredients of a composition to be mixed with a coffee extract. It may be in dry form, e.g. as a powder, or in liquid form, and may be packed in any suitable way, e.g. in a sachet, bottle or can. It should be formulated such that the microorganism and/or enzyme will not ferment or react with other ingredients during storage. This may be achieved e.g. by formulating the composition as a dry powder, and/or by encapsulating the microrganism and/or enzyme so that the microorganisms and/or enzyme will only be released when the composition is mixed with coffee extract or during digestion.

The at least two parts may be packed together in any suitable way. They may e.g. be packed in a combined container wherein the parts are kept physically separated during storage and mixed when the container is opened, or they may be packed in separate containers which are sold together for the preparation of a beverage.

Beverage Powder

In one embodiment the invention relates to a beverage powder comprising: a) a dried coffee extract; and b) a microorganism and/or an enzyme capable of hydrolysing chlorogenic acids to generate phenolic acids.

A beverage powder according to the invention is a powder to be used for the preparation of a beverage by dissolving or suspending the powder in a liquid, e.g. water or milk. The beverage to be prepared from the powder may e.g. be black coffee, café latte, café macchiato, cappuccino, or any other coffee based beverage.

The dried coffee extract may e.g. be a conventional pure soluble coffee powder, e.g. a spray dried or freeze dried coffee extract. Pure soluble coffee powders are readily available and extensively described in the art.

The microorganism and/or enzyme is present in a dry powdered form, e.g. as a freeze dried powder. The microorganism and/or enzyme may be encapsulated.

The beverage powder should be formulated such that the microorganism and/or enzyme will not ferment or react with the coffee extract and/or other ingredients during storage.

In a preferred embodiment of the invention a beverage powder comprises a composition to be mixed with a coffee extract as described herein in a dry from. In a more preferred embodiment of the invention a beverage powder comprises a creamer.

The beverage powder may comprise any other ingredient suitable for preparing the desired beverage. Suitable ingredients are well known in the art, and may e.g. be sugars, artificial sweeteners, emulsifiers, stabilisers, thickeners, flowing agents, colours, flavours, aromas, and the like. Suitable artificial sweeteners include saccharin, cyclamates, L-aspartyl based sweeteners such as aspartame, and mixtures of these. Suitable emulsifiers include monoglycerides, diglycerides, lecithin, diacetyl tartaric acid esters of mono-diglycerides (data esters), emulsifying starches and mixtures thereof. Suitable stabilisers include dipotassium phosphate and sodium citrate. A suitable flowing agent is sodium silica aluminate. In one embodiment the beverage powder comprises milk protein and/or vegetable protein. In another embodiment the beverage powder comprises milk fat or vegetable fat. In a further embodiment the beverage powder comprises a sweetener.

Use of Products of the Invention

The products of the invention may be used to enhance antioxidant capacity in vivo in a human or animal consuming a beverage prepared from the products of the invention, e.g. by inducing detoxifying enzymes such as gluthathione-S-transferase (GST) and by increasing the Nrf2-mediated gene expression pathway. Increased Nrf2 activity associated genes have been reported to enhance detoxification and to stimulate the endogenous defence against oxidative stress.

The products of the invention may be used to decrease inflammation, e.g. by reducing the prostaglandin E2 level.

Many health problems and disorders are related to oxidative stress and inflammation. The products of the invention may be used to treat or prevent such problems or disorders in a human or animal consuming a beverage prepared from the products of the invention. Relevant problems and disorder are e.g. skin disorders, e.g. photo-damage caused by UV-radiation, atopic dermatitis, eczema, scaling, itching, allergic symptoms; brain disorders; inflammation; obesity; and cancer, e.g. skin cancer and lung cancer.

The products of the invention may further be used as anti-diabetic agents, e.g. by reducing blood glucose levels, and/or increasing blood levels of leptin, insulin and/or c-peptide; as bone remodelling agents, e.g. by increasing bone mineral density, e.g. by increasing serum levels of estrogen and/or progesterone and/or alkaline phosphatase activity; as anti-metastatic agents, e.g. with anti-angiogenic effect.

EXAMPLES

Example 1

Treatment of NESCAFE PROTECT® with *Lactobacillus johnsonii* Fresh Cells

Cells of *L. johnsonii* (CNCM I-1225) were grown (7.0 E08 cfu/ml) and centrifuged (5000 g, 10 min), the pellets were resuspended in phosphate buffer (50 mM, pH 7.0) at a concentration of 0.61 g/ml. 30 mg/ml of NESCAFE PROTECT® (a dried co-extract of green and roasted coffee beans) was added and the mixture was incubated at 37° C. Samples were withdrawn at different reaction times, centrifuged (3000 g, 5 min) and filtered through 0.45 µm pore size syringe filters (Millipore SLHA 025 BS) and analysed by HPLC.

A reaction control was run in parallel under the same reaction conditions but without bacteria.

Treatment of NESCAFE PROTECT® with *Lactobacillus Johnsonii* Extract (Lysed cells)

Cells of *L. johnsonii* (CNCM I-1225) were grown (7.0 E08 cfu/ml) and centrifuged (5000 g, 10 min), the pellets were resuspended in phosphate buffer (50 mM, pH 7.0) at a concentration of 0.61 g/ml. The cells were then lysed using the glass-beads method. 600 µl of cells preparation were put in screw-cap tubes and 600 µl of glass-beads were added at 0° C. The tubes were then put into a Mini-Beadbeater for 1 min of intense shaking, cooled in ice, and put another 1 min in the Mini-Beadbeater. The crude cell extract was then added to 900 µl of a solution of NESCAFE PROTECT® (30 mg/ml, phosphate buffer pH 7.0) and the mixture was incubated at 37° C. Samples were withdrawn at different reaction times, centrifuged (3000 g, 5 min), filtered through 0.45 µm pore size syringe filters (Millipore SLHA 025 BS) and analysed by HPLC.

Treatment of NESCAFE PROTECT® with Spray-Dried Preparation of *Lactobacillus johnsonii*

30 mg of NESCAFE PROTECT® were dissolved in 1 ml phosphate buffer (50 mM, pH 7.0) or in 1 ml water. To this solution, 10 mg of a spray-dried preparation of *Lactobacillus johnsonii* (CNCM I-1225) (3.3 E9 cfu/g) were added. The mixture was then incubated at 37° C. and samples were withdrawn at different reaction times. After centrifugation (3000 g, 5 min) and filtration (0.45 µm pore size syringe filters, Millipore SLHA 025 BS) the samples were analysed by HPLC.

Treatment of Green Coffee Extract with a Spray-Dried Preparation of *Lactobacillus johnsonii* (CNCM I-1225)

30 mg of a dried green coffee extract was dissolved in 1 ml phosphate buffer (50 mM, pH 7.0) or in 1 ml water. To this solution, 10 mg of a spray-dried preparation of *Lactobacillus johnsonii* (3.3 E9 cfu/g) was added. The mixture was then incubated at 37° C. and samples were withdrawn at different reaction times. After centrifugation (3000 g, 5 min) and filtration (0.45 µm pore size syringe filters, Millipore SLHA 025 BS) the samples were analysed by HPLC.

Treatment of NESCAFE® with a concentrated preparation of *Lactobacillus johnsonii* (CNCM I-1225)

400 mg of NESCAFE SPECIAL FILTRE® (a dried extract of roasted coffee beans) were dissolved in 1 ml of boiling water and the solution was cooled to 37° C. at room temperature. To 250 µl of this coffee solution, different amounts of concentrated preparation of *Lactobacillus johnsonii* (50 µl, 100 µl, 350 µl, 750 µl) were added and the volume was adjusted to 1 ml with water. The mixtures were than incubated at 37° C. for 2 h and 4 h. After centrifugation (3000 g, 5 min) and filtration the samples were analysed by HPLC.

HPLC Analysis

Coffee samples were diluted to 1% w/w and analyzed by RP-HPLC on a CC 250/4 Nucleosil 100-5-C18 column (Macherey-Nagel). The eluent system was Millipore water, 0.1% TFA and $CH_3CN$ at a flow rate of 1 mL/min. The method allowed the simultaneous determination of caffeoyl quinic acids (CQA), feruloyl quinic acids (FQA), di-caffeoyl quinic acids (diCQA), feruloyl quinic acid-lactones, caffeic acid (CA) and ferulic acid (FA) (absorbance at 325 nm) using external standard calibration curves. Results were expressed relative to the reference at time 0 (t0) or to the reference at the same time without bacteria.

Antioxidant Responsive Element (ARE) Luciferase Assay

The pGL-8×ARE which contains eight copies of the ARE present in rat glutathione-S-transferase A2 (GSTA2) along with the pcDNA3.1 plasmid containing the neomycin selectable marker was stably transfected into human MCF7 cells (Wang et al., Cancer Res. 66, 10983-10994, 2006). ARE (antioxidant-responsive element) is the binding site of the transcription factor Nrf2 which regulates the genes involved in detoxification and endogenous defence against oxidative stress. The plasmid pGL-8×ARE contains a luciferase gene downstream of the eight Nrf2 binding sites that allows monitoring Nrf2 activity.

For treatment with coffee, the AREc 32 cells were seeded in 96-well microtiter plates in DMEM growth medium. After treatment for 24 h with the different coffees, firefly luciferase activity was determined.

Protein Expression

Primary hepatocytes were obtained by perfusion of the liver of Sprague-Dawley rats with a collagenase solution (Sidhu et al., Arch. Biochem. Biophys. 301, 103-113, 1993).

Cell viability, estimated by Trypan Blue exclusion test, was found to range between 90-95%. The cells were seeded at a density of $1.5 \times 10^5$ cells/cm$^2$ on 60 mm plastic tissue culture dishes in 3 ml of William's medium supplemented with 2 mM L-glutamine, 10 mM Hepes pH 7.4, ITS+, 15000 U Penicillin/Streptomycin, 100 nM Dexamethasone and 5% Fetal bovine serum (Hi-clone). Hepatocytes were allowed to attach for two hours and then washed with EBSS to remove debris and unattached cells. Fresh serum-free medium containing 25 nM of dexamethasone was added and an overlay of matrigel (233 g/ml) was then applied. Fresh matrigel was added to the cultures every two days following medium change. To study the effect of coffee on detoxifying enzymes and antioxidant protein expression, the test material was added to the culture media 24 hours after cell seeding for a period of 48 hours before protein extraction and western blot analysis (Cavin et al., Food Chem Tox. 46, 1239-48, 2008).

Prostaglandin E2 Formation Assay

Human colon HT-29 cells were treated with the different coffees for 15 h followed by a co-incubation of 6 h together with a pro-inflammatory agent TNF-α (10 ng/ml). Analysis of the PGE2 production in HT-29 cells was determined using a competitive enzyme immunoassay (EIA) (Cavin et al., BBRC 327, 742-49, 2005).

Results

Hydrolysis of Chlorogenic Acids to Generate Phenolic Acids

Experiment 1: Treatment of NESCAFE PROTECT® with *L. johnsonii* fresh cells with varying reaction times and amount of cell preparation. Results are shown in Table 1.

TABLE 1

Results of experiment 1.

| Time (h) | 6 | 24 | 6 | 24 | 6 | 24 |
|---|---|---|---|---|---|---|
| Cell preparation (uL) | 750 | 750 | 350 | 350 | 100 | 100 |
| Concentration in % relative to untreated reference at t = 0 | | | | | | |
| CQA | 3 | 0 | 14 | 3 | 39 | 15 |
| FQA | 8 | 0 | 17 | 4 | 42 | 17 |
| diCQA | 0 | 0 | 0 | 0 | 23 | 2 |
| CA | 13215 | 13238 | 14282 | 15981 | 10111 | 13661 |
| FA | 7776 | 8845 | 7234 | 8861 | 4594 | 6691 |
| Mass balance (mmol/g dry matter) | | | | | | |
| Chlorogenic acids consumed | 0.20 | 0.21 | 0.18 | 0.20 | 0.13 | 0.17 |
| CA and FA formed | 0.20 | 0.20 | 0.21 | 0.24 | 0.14 | 0.20 |

Experiment 2: Treatment of NESCAFE PROTECT® with *L. johnsonii* extract (lysed cells) with varying reaction times and amount of cell preparation. Results are shown in Table 2.

TABLE 2

Results of experiment 2.

| Time (h) | 2 | 2 | 6 | 6 |
|---|---|---|---|---|
| Cell preparation (uL) | 350.0 | 100.0 | 350.0 | 100.0 |
| Concentration in % relative to untreated reference at t = 0 | | | | |
| CQA | 10 | 32 | 6 | 14 |
| FQA | 15 | 36 | 11 | 18 |
| diCQA | 1 | 8 | 1 | 1 |
| CA | 13901 | 10729 | 16300 | 12581 |
| FA | 7771 | 5581 | 9720 | 6960 |

Experiment 3: Treatment of NESCAFE PROTECT® with spray-dried preparation of *Lactobacillus johnsonii*. Results are shown in Table 3.

TABLE 3

Results of experiment 3.
CQA, FQA, CA and FA are given as % relative to untreated control at t = 0.

| Time (h) | 2 | 6 | 24 |
|---|---|---|---|
| CQA | 73 | 67 | 32 |
| FQA | 82 | 60 | 34 |
| CA | 3598 | 6140 | 7879 |
| FA | 1109 | 2183 | 3686 |

Experiment 4: Treatment of green coffee extract with a spray-dried preparation of *Lactobacillus johnsonii*. Results are shown in table 4.

TABLE 4

Results of experiment 4.
CQA, FQA, CA and FA are given as % relative to untreated control at t = 0.

| Time (h) | 4 | 6 | 16 | 24 |
|---|---|---|---|---|
| CQA | 77 | 69 | 58 | 50 |
| FQA | 79 | 71 | 48 | 52 |
| diCQA | 67 | 53 | 32 | 20 |
| CA | 2673 | 3762 | 5182 | 6145 |
| FA | 961 | 1429 | 1963 | 2432 |

Experiment 5: Treatment of NESCAFE® with a concentrated preparation of *Lactobacillus johnsonii*. Results are shown in table 5.

TABLE 5

Results of experiment 5.
CQA, FQA, CA and FA are given as % relative to untreated control at t = 0.

| Time (h) | Cell amount | | | | | | | |
|---|---|---|---|---|---|---|---|---|
| | 50 µL/ 1 mL 2 | 100 µL/ 1 mL 2 | 350 µL/ 1 mL 2 | 750 µL/ 1 mL 2 | 50 µL/ 1 mL 4 | 100 µL/ 1 mL 4 | 350 µL/ 1 mL 4 | 750 µL/ 1 mL 4 |
| CQA | 92 | 80 | 46 | 25 | 76 | 60 | 33 | 17 |
| FQA | 90 | 82 | 61 | 41 | 89 | 74 | 53 | 37 |
| diCQA | 86 | 68 | 23 | 6 | 75 | 56 | 15 | 6 |
| CA | 1737 | 2885 | 5752 | 7292 | 1763 | 2803 | 4491 | 5514 |
| FA | 1509 | 2468 | 5327 | 7586 | 786 | 1266 | 2408 | 3281 |

Table 6 show the absolute concentration of a number of compounds in two different samples of extracts of green coffee beans that have not been treated to hydrolyse chlorogeninc acids (control samples).

TABLE 6

Composition of untreated green coffee extracts (control samples).
Concentration is given in milligram per gram of dry matter.

| | A | B |
|---|---|---|
| 3-caffeoyl quinic acid | 13.88 | 15.57 |
| 4-caffeoyl quinic acid | 17.58 | 20.08 |
| 5-caffeoyl quinic acid | 81.16 | 85.45 |
| Sum CQA | 112.62 | 121.10 |
| 3-feruloyl quinic acid | 0.00 | 0.00 |
| 4-feruloyl quinic acid | 3.29 | 4.41 |
| 5-feruloyl quinic acid | 17.70 | 19.77 |
| Sum FQA | 20.99 | 24.18 |
| CA | 0.39 | 0.47 |
| FA | 0.25 | 0.23 |
| 3-caffeoyl quinic acid lactone | 0.00 | 0.00 |
| 4-caffeoyl quinic acid lactone | 0.00 | 0.00 |
| Sum Lactones | 0.00 | 0.00 |
| 3,4-dicaffeoyl quinic acid | 6.80 | 4.34 |
| 3,5-dicaffeoyl quinic acid | 5.53 | 8.35 |
| 4,5-dicaffeoyl quinic acid | 0.12 | 8.85 |
| sum dicaffeoyl quinic acid | 12.45 | 21.55 |

Protein Expression

In rat primary hepatocytes, NESCAFE RED CUP® (extract of roasted coffee beans) at 200 ug/ml produced after 48 h of treatment no increase in the protein expression of GST subunits (GSTA4, GSTP1) and Heme-Oxygenase-1 (HO-1) and weak inductions of GSTP1 and HO-1 expressions at 400 ug/ml by western blot. In contrast, a stronger induction of the different protein expressions was observed with NESCAFE PROTECT® treated with *L. johnsonii* at both 200 ug/ml and 400 ug/ml on GSTA4, GSTP1 and HO-1). Results are shown as Western Blot gels in FIG. 1.

Figure 2:
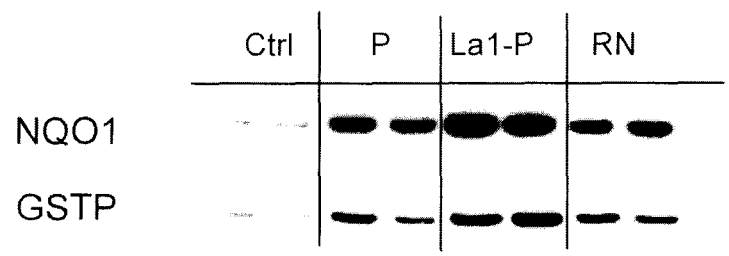
FIG. 2: Western Blot showing induction of detoxifying enzyme expression (GSTP1; NQO1) in the liver of male rats fed in their diet for 2 weeks with 5% of NESCAFE RED CUP® (extract of roasted coffee beans) not treated to hydrolyse chlorogenic acids (RN), NESCAFE PROTECT® (a co-extract of green and roasted coffee beans) not treated to hydrolyse chlorogenic acids (P); and NESCAFE PROTECT® treated with *Lactobacillus johnsonii* (La1-P). For details see example 1.

Data obtained in the liver of male rats fed in their diet for 2 weeks with 5% of NESCAFE RED CUP® versus NESCAFE PROTECT® and NESCAFE PROTECT® treated with *L. johnsonii* confirmed the effects observed in rat primary hepatocytes. Strongest induction of detoxifying enzyme expression (GSTP1; NQO1) was found with the NESCAFE PROTECT® treated with *L. johnsonii* as compared to untreated NESCAFE PROTECT® (GSTP1; NQO1) and untreated NESCAFE RED CUP® (GSTP1; NQO1). Results are shown as Western Blot gels in FIG. 2.

Antioxidant Responsive Element (ARE) Luciferase Assay

Human breast cancer cells (AREc32) stably transfected with several copies of the rat GSTA2-ARE reporter construct was used to demonstrate the activation of Nrf2-ARE pathway by coffee. Green coffee extract not treated to hydrolyse chlorogenic acids, and different green coffee extract treated with *L. johnsonii* for 24 h produced a dose-dependent increase in Nrf2-luciferase reporter activity (see table 7).

TABLE 7

Induction of Nrf2 activity by coffee
(firefly luciferase activity, AU).

| Coffee extract ug/ml | Green coffee extract untreated | Green coffee extract 1 treated | Green coffee extract 2 treated | Green coffee extract 3 treated |
|---|---|---|---|---|
| 0 | 0 | 0 | 0 | 0 |
| 200 | 0.3 +/− 0.1 | 15.2 +/− 1.5 | 22.1 +/− 1.6 | 22.6 +/− 2.4 |
| 300 | 0.8 +/− 0.1 | 29.0 +/− 3.0 | 40.5 +/− 1.6 | 32.1 +/− 6.0 |
| 400 | 1.0 +/− 0.1 | 40.4 +/− 6.6 | 59.3 +/− 1.9 | 47.3 +/− 3.4 |
| 600 | 2.0 +/− 0.2 | 77.7 +/− 10.5 | 90.4 +/− 0.7 | 80.4 +/− 8.2 |
| 800 | 2.8 +/− 0.1 | 77.3 +/− 4.9 | 80.7 +/− 7.3 | 96.2 +/− 4.1 |

Prostaglandin E2 Formation Assay

Potential anti-inflammatory effect of green coffee extract treated with *L. johnsonii* was assessed in human colon HT-29 cells. Following treatment with a pro-inflammatory agent TNF-α, prostaglandin E2 ($PGE_2$) level is induced in colon cells. In this study, cells were pre-treated for 24 h with different coffee extracts (green coffee extract not treated to hydrolyse chlorogenic acids, and different green coffee extract treated with *L. johnsonii* for 24 h). TNF-α (10 ng/ml) was added in the last 6 h of the experiment. Data (see table 8) showed a clear dose-dependent decrease by coffees of $PGE_2$ formation as compared to control cells treated with TNF-α

TABLE 8

Decrease of $PGE_2$ formation as a result of coffee extract treatment
as compared to control cells treated with TNF-α (AU).

| Coffee extract ug/ml | Green coffee extract untreated | Green coffee extract 1 treated | Green coffee extract 2 treated |
|---|---|---|---|
| 0 | 100 +/− 9 | 100 +/− 9 | 100 +/− 9 |
| 50 | 110 +/− 10 | 18 +/− 2 | 43 +/− 5 |
| 100 | 85 +/− 9 | 6 +/− 0.9 | 10 +/− 1.1 |
| 200 | 80 +/− 8 | 1 +/− 0.1 | 1 +/− 0.2 |

Example 2

Coffee Samples

Green coffee extract from 100% Robusta green beans
NESCAFE PROTECT®, a dried co-extract of green and roasted coffee beans

| Enzymes and cells | |
|---|---|
| Microorganisms | Culture medium |
| Lactobacillus johnsonii (CNCM I-1225) | MRS |
| Bifidobacterium lactis BB12 (CNCM I-3446) | MRS + cysteine |
| Bifidobacterium longum BB536 (ATCC BAA-999) | MRS + cysteine |

Chlorogenate esterase (24 U/g), derived from *Aspergillus japonicus* (Kikkoman, Japan).
Tannase from *Aspergillus oryzae* (Kikkoman, Japan)

Preparation of Bacteria Cells

Tested strains were harvested (centrifugation at 5000 g for 10 min) after having well reached stationary phase, corresponding to 16 hours of incubation in culture medium at 37° C. in anaerobic atmosphere without agitation. For a first activation of the strains, frozen stock cultures were inoculated in fresh media and grown overnight. This pre-culture was used to inoculate the culture.

Treatment of Coffee Extracts with Bacteria Cells

After culture of bacteria and centrifugation, the pellets were resuspended in phosphate buffer (pH 7.0) at a concentration of 0.61 g/ml. To 200 μl of this cells preparation, 800 μl of a coffee solution (3%) was added and the mixture was incubated at 37° C. for 4 h, 16 h and 24 h.

Incubation of Coffee Extracts with Chlorogenate Esterase

A solution of chlorogenate esterase (25 mg) in 200 μl phosphate buffer (pH 7.0) was added to 800 μl of a coffee solution (3%). The mixture was then incubated at 37° C. for 4 h, 16 h and 24 h. After reaction time, the enzymatic activity was stopped by heat treatment (3 min, 90° C.) and the mixture was filtered before analysis.

ARE Luciferase Assay

As in example 1

Results

Human breast cancer cells (AREc32) stably transfected with several copies of the rat GSTA2-ARE reporter construct was used to demonstrate the activation of the antioxidant Nrf2-ARE pathway by coffee. Green coffee extract not treated to hydrolyse chlorogenic acids (untreated), green coffee extract treated with *Lactobacillus johnsonii*(Lj) for 24 h, green coffee extract treated with *Bifidobacterium lactis* (Bl) for 24 h, and green coffee extract treated chlorogenate esterase (CE) for 4 h, all produced a dose-dependent increase in Nrf2-luciferase reporter activity (table 9).

TABLE 9

Nrf2-luciferase reporter activity of untreated and treated coffee extracts (AU).

| Coffees mg/ml | Green coffee untreated | Green coffee treated with Lj | Green coffee treated with Bl | Green coffee treated with CE |
|---|---|---|---|---|
| 0 | 0 | 0 | 0 | 0 |
| 100 | 0.3 +/- 0.1 | 0.5 +/- 0.1 | 0.3 +/- 0.1 | 1.0 +/- 0.1 |
| 200 | 0.8 +/- 0.1 | 1.0 +/- 0.1 | 1.1 +/- 0.1 | 2.1 +/- 0.2 |
| 400 | 1.0 +/- 0.1 | 5.2 +/- 0.4 | 3.1 +/- 0.3 | 8.2 +/- 1.4 |
| 600 | 2.0 +/- 0.2 | 11.1 +/- 0.5 | 7.2 +/- 1 | 11.3 +/- 1.4 |

Green coffee extracts were treated with different microrganisms and chlorogenate esterase to hydrolyse chlorogenic acids. Results are shown in table 10.

TABLE 10

Composition of green coffee extracts as a result of treatments.
CQA, FQA, CA and FA are given as % relative to untreated control at t = 0.

| | Lactobacillus Johnsonii | | | Bifidobacterium lactis | | | Chlorogenate esterase | | |
|---|---|---|---|---|---|---|---|---|---|
| time (h) | 4 | 16 | 24 | 4 | 16 | 24 | 4 | 16 | 24 |
| CQA | 42 | 15 | 12 | 96 | 79 | 74 | 3 | 2 | 2 |
| FQA | 49 | 15 | 15 | 33 | 12 | 6 | 73 | 24 | 23 |
| diCQA | 35 | 6 | 3 | 85 | 70 | 64 | 0 | 0 | 0 |
| CA | 12505 | 17148 | 18107 | 1521 | 4182 | 5283 | 18917 | 17275 | 18318 |
| FA | 4607 | 7192 | 7597 | 5020 | 6970 | 7105 | 2620 | 5685 | 6293 |

NESCAFE PROTECT® was treated with different microrganisms and chlorogenate esterase to hydrolyse chlorogenic acids. Results are shown in table 11.

TABLE 11

Composition of NESCAFE PROTECT ® as a result of treatments.
CQA, FQA, CA and FA are given as % relative to untreated control at t = 0.

| | Lactobacillus Johnsonii | | | Bifidobacterium lactis | | | Chlorogenate esterase | | |
|---|---|---|---|---|---|---|---|---|---|
| time (h) | 4 | 16 | 24 | 4 | 16 | 24 | 4 | 16 | 24 |
| CQA | 33 | 13 | 13 | 97 | 81 | 80 | 5 | 3 | 3 |
| FQA | 42 | 21 | 20 | 54 | 23 | 20 | 54 | 15 | 14 |
| diCQA | 18 | 2 | 2 | 91 | 72 | 67 | 0 | 0 | 1 |
| CA | 7942 | 9429 | 9933 | 968 | 2258 | 2840 | 10879 | 10198 | 10750 |
| FA | 4051 | 5226 | 5504 | 3065 | 4518 | 5144 | 2794 | 5140 | 5518 |

Example 3

Gastric Small-Intestinal Model (TIM)

The gastric small-intestinal model, TIM-1, comprises four connected compartments that represent the stomach, duodenum, jejunum and ileum, respectively. Each compartment consists of a glass outer wall with a flexible inner wall. The flexible wall is surrounded by water at 37° C. to squeeze the walls, which ensures mixing of the food with the secreted enzymes by peristaltic movements in the gastro-intestinal tract.

The experiments in the model were performed under average physiological conditions of the gastro-intestinal tract. During the experiments, the temperature was kept at 37° C. and salivary, gastric, biliary, and pancreatic secretions were simulated. The digestion process in the model was monitored for 6 h. During the first 3.5 h, the gastric content was gradually delivered into the small intestine "pyloric valve". At the end of the experiment, approximately 80% of the small-intestine content was gradually delivered into the "large intestine" via the ileocaecal valve. Gastric pH gradually decreased from 6.5 to 2.0 in approximately 5 h by the secretion of 1 M HCl; the pH of the small intestinal contents was maintained at 6.5 in the duodenum, 6.8 in the jejunum and 7.2 in the ileum. Products of digestion and water were absorbed from the jejunal and ileal compartments by pumping dialysis liquid through hollow fiber membranes with a molecular weight cut-off of approximately 5 000 Dalton.

Simulation of Coffee Extract Digestion 4.5 g of NESCAFE PROTECT® (a co-extract of green and roasted coffee beans) were dissolved in 310 ml acetate buffer (20 mM, pH 6.5). After addition of 10 ml start residue (5 g of pepsin and 5 g of lipase enzyme solutions) the solution was injected into the gastric compartment of TIM. During digestion, total dialysate was collected for 0-2, 2-4, and 4-6 h. After 6 h experiment, the residues from the compartments of the stomach, duodenum, jejunum and ileum were analysed to calculate the mass balance of chlorogenic acids. The samples were passed through a 0.45 μm pore size syringe filters (Millipore SLHA 025 BS) and analysed by HPLC as described in Example 1. For the experiment with *Lactobacillus johnsonii* (CNCM I-1225), 310 ml of acetate buffer solution (20 mM, pH 6.5) containing a total of 3.3 E9 cfu of spray-dried preparation of *L. johnsonii*, were put into the gastric compartment after addition of 10 ml start residue. 10 ml of acetate buffer containing 4.5 g Nescafe Protect was then injected by a syringe into the gastric compartment 15 min after starting digestion simulation. During digestion, total dialysate was collected for 0-2, 2-4 and 4-6 h after passage through the semi-permeable hollow-fiber membranes connected to the jejunal and ileal compartments. Total ileal delivery was collected for 0-2; 2-4 and 4-6 h. Aliquots (1 ml) were taken from gastric compartment directly after addition of NESCAFE PROTECT® and at time point 1 h. After 6 h, the residues from the compartments of the stomach, duodenum, jejunum and ileum were analysed by HPLC to calculate the mass balance of 5-caffeoyl quinic acid. Similar trials were conducted with NESCAFE COOL® (an extract of roasted coffee with creamer and sweetener) and with a normal filter brew of roast and ground coffee with added creamer, and with commercially available 5-caffeoyl quinic acid (5-CQA).

Results

The percentage of 5-caffeoyl quinic acid (5-CQA) hydrolysed during the experiments with addition of *L. johnsonii* is shown in table 12. No hydrolysis of 5-caffeoyl quinic acid (5-CQA) was observed in control experiments with no addition of *L. johnsonii*.

TABLE 12

Hydrolysis of 5-CQA in coffee extracts and pure 5-CQA as determined in the TIM model (% hydrolysed of total 5-CQA present in the samples).

| Product | % hydrolysis of 5-CQA |
|---|---|
| 5-CQA | 48 |
| NESCAFE PROTECT ® | 34 |
| NESCAFE COOL ® | 79 |
| Filter brewed roasted and ground coffee with Creamer | 53 |

The invention claimed is:

1. A beverage powder comprising:
   a dried coffee extract; and
   a component selected from the group consisting of a microorganism, an enzyme capable of hydrolysing caffeoyl quinic acid and diesters to generate caffeic acid, and combinations thereof.

2. The beverage powder of claim 1 comprising a creamer.

3. The beverage powder of claim 1 comprising a sweetener.

4. The beverage powder of claim 1 comprising a component selected from the group consisting of milk protein, milk fat, and combinations thereof.

5. The beverage powder of claim 1, wherein the microorganism capable of hydrolysing caffeoyl quinic acid and diesters to generate caffeic acid is a lactic acid bacteria.

6. A method for enhancing antioxidant capacity in vivo in a human or animal comprising the step of consuming a beverage prepared from a beverage powder comprising:
   a dried coffee extract; and
   a component selected from the group consisting of a microorganism, and an enzyme capable of hydrolysing caffeoyl quinic acid and diesters to generate caffeic acid, and combinations thereof.

* * * * *